(12) United States Patent
Ikeda et al.

(10) Patent No.: US 7,717,894 B2
(45) Date of Patent: May 18, 2010

(54) LIQUID-ABSORBENT SHEET AND METHOD FOR PRODUCING THE SAME

(75) Inventors: Hideki Ikeda, Fuji (JP); Masaki Okada, Fuji (JP)

(73) Assignees: Oji Paper Co., Ltd., Tokyo (JP); Oji Kinocloth Co., Ltd., Shizuoka-ken (JP)

( * ) Notice: Subject to any disclaimer, the term of this patent is extended or adjusted under 35 U.S.C. 154(b) by 461 days.

(21) Appl. No.: 11/546,657

(22) Filed: Oct. 11, 2006

(65) Prior Publication Data

US 2007/0088301 A1 Apr. 19, 2007

(30) Foreign Application Priority Data

Oct. 18, 2005 (JP) ............................. P2005-302562

(51) Int. Cl.
*A61F 13/15* (2006.01)
(52) U.S. Cl. .............................. 604/385.101; 604/366; 604/367; 604/368; 604/374; 604/375; 604/379
(58) Field of Classification Search ................. 604/366, 604/367, 368, 374, 375, 379, 385.101
See application file for complete search history.

(56) References Cited

U.S. PATENT DOCUMENTS 4,655,757 A * 4/1987 McFarland et al. .......... 604/366

FOREIGN PATENT DOCUMENTS

| JP | 08-107910 | 4/1996 |
| JP | 2000-135797 | 5/2000 |
| JP | 2002-035036 | 2/2002 |
| WO | WO 01/18302 A1 | 3/2001 |
| WO | WO 2005/061120 A1 | 7/2005 |

OTHER PUBLICATIONS

Office Action issued in counterpart Chinese Patent Application No. 200610141194.2, mailed Nov. 13, 2009.

\* cited by examiner

*Primary Examiner*—Jacqueline F. Stephens
(74) *Attorney, Agent, or Firm*—Knobbe, Martens, Olson & Bear, LLP

(57) ABSTRACT

A liquid-absorbent sheet containing: a liquid-absorbent surface material mainly containing a pulp; a liquid-absorbent nonwoven fabric; a liquid-absorbent rear material mainly containing a pulp; and a super absorbent polymer; wherein the super absorbent polymer is disposed at least between the liquid-absorbent surface material and the liquid-absorbent nonwoven fabric as an A layer and between the liquid-absorbent nonwoven fabric and the liquid-absorbent rear material as a B layer, the super absorbent polymer being contained in a total amount of 200 to 400 g/m$^2$, which is allocated in the A layer at 30 to 50% by mass, the liquid-absorbent nonwoven fabric layer at 0 to 40% by mass, and the B layer at 30 to 70% by mass, and the content ratio of the super absorbent polymer in the A layer is less than or equal to the content ratio of the super absorbent polymer in the B layer.

5 Claims, 1 Drawing Sheet

LIQUID-ABSORBENT SHEET AND METHOD FOR PRODUCING THE SAME

CROSS-REFERENCE TO RELATED APPLICATION

This application claims priority under 35 U.S.C. 119(a)-(d) to Japanese Patent Application No. 2005-302562, filed Oct. 18, 2005, the entire contents of which are incorporated herein by reference.

BACKGROUND OF THE INVENTION

1. Field of the Invention

The present invention relates to a liquid-absorbent sheet that can rapidly absorb and diffuse a liquid excreted from the human body such as urine or menstrual blood, the sheet having a structure for holding the liquid, and a method for producing the same. In particular, the present invention relates to a liquid-absorbent sheet available for paper diapers, sanitary napkins, or the like, and a method for producing the same. In more particular terms, the present invention relates to a liquid-absorbent sheet that is thin and has a high absorbent rate with less wet-back so as to effectively absorb and hold a liquid excreted from the human body.

2. Description of the Related Art

Various absorbent articles that absorb body fluid such as urine or menstrual blood have been known. The absorbent articles usually include a liquid-permeable top sheet, a liquid-impermeable back sheet, and an absorbent body disposed between the top sheet and the back sheet. Such absorbent articles are typified by disposable paper diapers and sanitary napkins and required to have a thin and lightweight shape and to have capabilities for rapidly absorbing and holding the body fluid such as urine or menstrual blood as much as possible without side leakage. Also, in recent years, such absorbent articles have been made compact, and therefore more stringently demanded to be thin. Moreover, such absorbent articles have been demanded to absorb the body fluid quickly with little return of the body fluid to the surface thereof at the skin side, and to be excellent in quality stability.

Such absorbent articles generally include an absorbent body in which a super absorbent polymer (hereinafter, abbreviated as SAP) is mixed in a pulverized pulp. Although the content of the SAP is generally increased so as to improve the absorbent rate, such an increase makes the absorbent body thicker, and thereby it becomes difficult to make the absorbent article compact. Moreover, although the SAP is usually added during pulverizing a sheet pulp to be mixed and pulverized with the pulp so as to reduce unevenness of the quality of obtained absorbent bodies, there is a case in which a part of the SAP is lost during the pulverizing step, and thereby the obtained absorbent bodies do not have sufficient absorbabilities. Moreover, when the thickness of the absorbent body is reduced by pressurization in addition to the above step so as to make the absorbent article thinner, the density of the SAP is increased, which suppresses the permeation of an absorbed liquid, and gaps of the SAP are reduced, which may make the liquid absorbability insufficient.

In order to solve the above problems, Patent Document 1 (Japanese Patent Application, First Publication No. 2002-35036) has proposed that perforating holes be formed on the surface of an absorbent body so as to improve the absorbability thereof. By forming such perforating holes, the absorbed liquid transfers to the back-sheet side at an initial stage, and so the absorbent rate is improved. Moreover, the absorbed liquid spreads around the perforating holes, and so the diffusion properties are also improved. However, when the perforating holes are formed, the qualities of obtained absorbent bodies vary widely, and a wet-back phenomenon in which the absorbed liquid returns through the perforating holes is caused.

On the other hand, Patent Document 2 (Japanese Patent Application, First Publication No. H 8-107910) has proposed an absorbent article in which the SAP is arranged to form parallel stripes. When the SAP is arranged to form parallel stripes, the diffusion properties and absorbability of the absorbent article are significantly improved, and so the absorbed liquid is rapidly absorbed and diffused. The reason for this is that vacant spaces produced in such an arrangement enable the SAP absorbing the liquid to swell. However, since the SAP is unevenly distributed, and so the absorbent article becomes thick, such an arrangement is not suitable for thinning the article.

Also, Patent Document 3 (Published Japanese translation No. 2003-508647 of PCT International Publication) discloses a method for producing an absorbent material that is used to form an absorbent article, the method aiming at stabilization of the liquid-absorbability of the absorbent article and reduction of the thickness thereof. In the method, the SAP is evenly dispersed in a pulp, and so the stability of the absorbability is excellent. Also, a press treatment is carried out so as to prepare the absorbent material as a thin sheet, and so the absorbent material is suitably available for reducing the thickness of the absorbent article. However, since the press treatment is carried out while adding water to the sheet, the SAP locating at the surface of the sheet is swollen, which may reduce the vacant space, and so the absorbent rate thereof may decrease.

SUMMARY OF THE INVENTION

The present invention includes the following aspects.

(1) A liquid-absorbent sheet containing: a liquid-absorbent surface material mainly containing a pulp; a liquid-absorbent nonwoven fabric; a liquid-absorbent rear material mainly containing a pulp; and a super absorbent polymer; in which the super absorbent polymer is disposed at least between the liquid-absorbent surface material and the liquid-absorbent nonwoven fabric as an A layer and between the liquid-absorbent nonwoven fabric and the liquid-absorbent rear material as a B layer, the super absorbent polymer being contained in a total amount of 200 to 400 $g/m^2$, which is allocated in A layer at 30 to 50% by mass, the liquid-absorbent nonwoven fabric layer at 0 to 40% by mass, and the B layer at 30 to 70% by mass, and the content ratio of the super absorbent polymer in the A layer is less than or equal to the content ratio of the super absorbent polymer in the B layer.

(2) A liquid-absorbent sheet according to (1), in which the liquid-absorbent nonwoven fabric is a hydrophilic air laid nonwoven fabric.

(3) A liquid-absorbent sheet according to (1), in which the liquid-absorbent nonwoven fabric contains a pulp and a thermally fusible synthetic fiber, and the content ratio of the thermally fusible synthetic fiber is 0.1 to 15% by mass with respect to the total mass of the nonwoven fabric excluding the super absorbent polymer.

(4) A liquid-absorbent sheet according to (1), in which the liquid-absorbent surface material layer and the A layer, or the B layer and the liquid-absorbent rear material layer are partially intermingled.

(5) A method for producing the liquid-absorbent sheet of (1), including: thermally fusing an interface between the liquid-absorbent surface material layer and the A layer and an interface between the liquid-absorbent rear material layer and the B layer using heating and pressing rollers.

BRIEF DESCRIPTION OF THE DRAWING

Some of the features and advantages of the invention have been described, and others will become apparent from the detailed description which follows and from the accompanying drawings, in which.

DETAILED DESCRIPTION OF THE INVENTION

Figure 1:
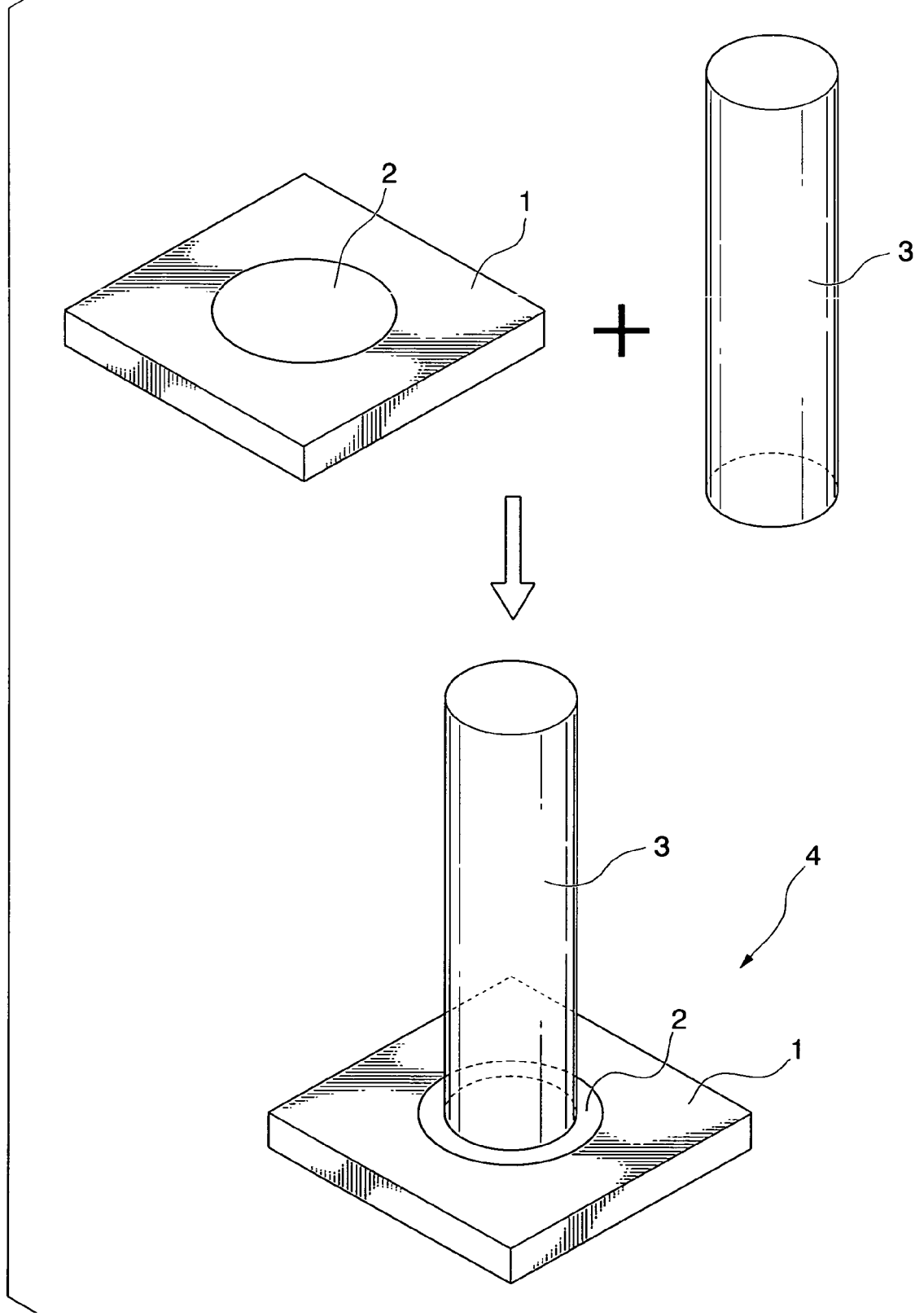
FIG. 1 is an elevational view indicating an apparatus used for evaluating the liquid absorbability of a liquid-absorbent sheet according to the present invention.

The present invention has as its object to solve the above-mentioned problems. That is, the present invention has as its object to provide a liquid-absorbent sheet which is thin and exhibits a rapid absorbent rate with less wet-back for the purpose of effectively absorbing and holding excreted body fluid, and to provide a method for effectively producing the liquid-absorbent sheet.

As a result of accumulated investigation carried out so as to solve the above-mentioned problems, the inventors of the present invention have found that a thin liquid-absorbent sheet with a rapid absorbent rate and less wet-back can be produced by making it a structure having at least five layers, that is, a liquid-absorbent surface material layer mainly containing a pulp, a liquid-absorbent nonwoven fabric layer, a liquid-absorbent rear material layer mainly containing a pulp, and at least two SAP layers containing a SAP, the SPA layers being disposed at least between the liquid-absorbent surface material layer and the liquid-absorbent nonwoven fabric layer as A layer and between the liquid-absorbent nonwoven fabric layer and the liquid-absorbent rear material layer as B layer, and completed the present invention.

In the following, particular preferred embodiments of the liquid-absorbent sheet according to the present invention will be explained in more detail. However, this detailed description is not intended to limit the enumerated claims, but to serve as particular examples thereof.

The liquid-absorbent sheet according to the present invention contains a liquid-absorbent surface material mainly containing a pulp; a liquid-absorbent nonwoven fabric; a liquid-absorbent rear material mainly containing a pulp; and a super absorbent polymer. The liquid-absorbent surface material forms a liquid-absorbent surface material layer. The liquid-absorbent nonwoven fabric forms a liquid-absorbent nonwoven fabric layer. The liquid-absorbent rear material forms a liquid-absorbent rear material layer. The super absorbent polymer forms SAP layers disposed at least between the liquid-absorbent surface material and the liquid-absorbent nonwoven fabric as A layer and between the liquid-absorbent nonwoven fabric and the liquid-absorbent rear material as B layer.

The liquid-absorbent surface material layer and the liquid-absorbent rear material layer composing the liquid-absorbent sheet according to the present invention also serve as anti-detaching layers for preventing the SAP layers (A and B layers) from becoming detached. In order that the liquid absorbability of the SAP layers is not suppressed, the liquid-absorbent surface material and the liquid-absorbent rear material are preferably a hydrophilic base material mainly containing a pulp, such as tissue, absorbent paper, nonwoven fabric, or the like, and examples thereof include cellulose fiber, such as wood pulp generally used for manufacturing paper, such as softwood or hardwood chemical pulp or mechanical pulp, recycled pulp, or the like. In addition to the cellulose fiber (pulp), a non-wood pulp such as hemp or cotton, a chemosynthetic pulp, a synthetic fiber such as polyester or rayon, or the like may be included in an amount that does not suppress the liquid absorbability of the SAP layers. When such a base material is used as the liquid-absorbent surface material composing the liquid-absorbent surface material layer, the liquid-absorbent surface material layer is made to be porous so as to promote liquid permeation. When such a base material is used as the liquid-absorbent rear material composing the liquid-absorbent rear material layer, the liquid absorbability and holding properties of the liquid-absorbent sheet become excellent.

The liquid-absorbent nonwoven fabric used for composing the liquid-absorbent nonwoven fabric layer of the liquid-absorbent sheet according to the present invention may be made from any materials provided that the materials have the liquid permeability and liquid absorbability, and examples thereof include nonwoven fabric made from a fiber such as rayon, polyethylene terephthalate, polypropylene, polyamide, acryl, polyvinyl alcohol, polyethylene, wool, cotton, hemp, pulp, glass, or the like, a blended fiber containing plural kinds thereof, using a suitable processing method such as a spun lace method, a spunbonding method, a thermal bonding method, a chemical bonding method, an air laid method, a melt-blown method, a needle punching method, a stitch bond method, or the like.

In the liquid-absorbent nonwoven fabric, a thermally fusible synthetic fiber such as a polyethylene (PE) fiber, a polypropylene (PP) fiber, a polyethylene terephthalate (PET) fiber, a polyamide fiber, a composite fiber of PE and PP, a composite fiber of PE and PET, a composite fiber of PP and PET, a composite of PET and PET, a composite fiber of polyamide and polyamide, or the like, is preferably contained so that the nonwoven fabric layer and the SAP layers are tightly adhered when the layers are heated and pressurized.

As the thermally fusible synthetic fiber, a composite fiber containing PP as a core component and PE as a sheath (shell) component (so-called core-sheath or core-shell type composite fiber) or the like is preferably used.

The thermally fusible synthetic fiber may be contained in such a way as to be deposited with a predetermined thickness on the surface of the nonwoven fabric base material composed of a pulp fiber or the like, or in such a way as to be mixed with the pulp fiber or the like to form a nonwoven fabric containing the thermally fusible synthetic fiber together with the pulp fiber or the like. The thermally fusible synthetic fiber may be used in combination of plural kinds thereof, or may be used in such a way that plural kinds thereof are separately laminated. Among these, a hydrophilic air laid nonwoven fabric made using the thermally fusible synthetic fiber together with a pulp or other vegetable fibers or the like are preferably used in view of the liquid permeability and the liquid absorbability.

It is preferable that the content of the thermally fusible synthetic fiber in the nonwoven fabric be 0.1 to 15% by mass, and more preferably 1 to 15% by mass, with respect to the total mass of the nonwoven fabric excluding the SAP content so as to prevent deterioration of the absorbed-liquid holding property and swelling property of the SAP. When the content of the thermally fusible synthetic fiber is less than 0.1% by mass, the thermal fusion may not be able to realize sufficient bonding force for composing the liquid-absorbent sheet. On the other hand, when the content of the thermally fusible synthetic fiber is more than 15% by mass, the liquid absorbability of the liquid-absorbent nonwoven fabric layer may become insufficient. As the thermally fusible synthetic fiber, one with a fiber length of approximately 3 to 51 mm and a fineness of approximately 1.1 to 7.7 dtex is preferably used.

In the liquid-absorbent nonwoven fabric layer, the SAP is contained in an amount of 0 to 40% by mass with respect to the total mass of the SAP without preventing liquid from transferring to B layer laminated on the liquid-absorbent rear material layer.

The SAP used in the present invention can absorb at least 20-fold fluid such as urine, body fluid, or the like, with respect to its own weight, and examples thereof include starch-based ones, cellulose-based ones, synthetic polymer-based ones, or the like, such as starch—acrylate graft copolymers, isobutylene—maleic acid copolymers, saponified starch—ethyl acrylate graft copolymers, saponified starch—methyl methacrylate graft copolymers, saponified starch—acrylonitrile copolymers, saponified starch—acrylamide graft copolymers, acrylate polymers such as sodium polyacrylates, polyethylene oxide cross-linked with acrylic acid, cross-linked sodium carboxymethyl celluloses, cross-linked polyvinyl alcohol—maleic acid anhydride copolymers, biodegradable polyaspartic acid cross-linked by amino acids, SAPs originating from microorganisms that are cultured products of Alcaligenes Latus, or the like. Among these, sodium polyacrylates are preferably used due to the excellent liquid-absorbability thereof. The form of the SAP used in the present invention is preferably granular, flake, pellet, short needle, chip, or the like, so as to be able to be evenly sprayed in a dry state, however the form is not limited to these.

Examples of a method for spraying the SAP include spraying methods using a slide equipped with a vibrator, screw type feeder, grid roll, or the like, methods using static electricity such as electrostatic coating, or the like.

The total content of the SAP contained in the liquid-absorbent sheet according to the present invention is 200 to 400 $g/m^2$, and preferably 200 to 350 $g/m^2$. When the total content of the SAP is less than 200 $g/m^2$, the liquid absorbability of the liquid-absorbent sheet becomes insufficient. On the other hand, when the total content of the SAP is more than 400 $g/m^2$; the total mass of the liquid-absorbent sheet becomes extremely large, and so the liquid-absorbent sheet cannot be thinned.

Also, the content ratio of the SAP in A layer disposed between the liquid-absorbent surface material layer and the liquid-absorbent nonwoven fabric layer is 30 to 50% by mass, with respect to the total mass of the SAP. The content ratio of the SAP in B layer disposed between the liquid-absorbent nonwoven fabric layer and the liquid-absorbent rear material layer is 30 to 70% by mass, with respect to the total mass of the SAP. The content ratio of the SAP included in the liquid-absorbent nonwoven fabric layer is 0 to 40% by mass, with respect to the total mass of the SAP. The content ratio of the SAP in A layer is less than or equal to that of the SAP in B layer.

When the content ratio of the SAP in A layer is less than 30% by mass, the amount of wet-back tends to increase. On the other hand, when the content ratio of the SAP in A layer is more than 50% by mass, the liquid-absorbent rate tends to decrease.

When the content ratio of the SAP in B layer is less than 30% by mass, although the initial liquid-absorbability is good, the total amount of the absorbed liquid tends to decrease. On the other hand, when the content ratio of the SAP in B layer is more than 70% by mass, the total amount of the absorbed liquid tends to decrease and the amount of wet-back tends to increase.

Moreover, when the content ratio of the SAP in B layer is less than that of the SAP in A layer, the absorbability of A layer tends to reach saturation, and so the absorbability of B layer tends not to be sufficiently and effectively demonstrated.

When the content ratio of the SAP in the liquid-absorbent nonwoven fabric is more than 40% by mass, the amount of wet-back tends to increase, and the liquid absorbability tends to become insufficient.

As described above, when the content ratio of the SAP is within the above-defined range, vacant spaces in A layer are maintained, the liquid passing through the vacant spaces is instantaneously held in the middle layer, that is, the liquid-absorbent nonwoven fabric layer, and then the held liquid smoothly transfers from the middle layer to B layer. Thus, the liquid-absorbent sheet that is thin and exhibits a rapid absorbent rate with less wet-back can be obtained.

The liquid-absorbent sheet according to the present invention can be produced according to the disclosure of Japanese Patent Application, First Publication No. 2000-135797, for example. In more detail, the SAP is sprayed to deposit on the liquid-absorbent rear material as B layer using a powder feeder. Then, the above-mentioned materials for the liquid-absorbent nonwoven fabric are mixed and laminated on B layer using a mat former or the like. Then, the SAP is sprayed on the liquid-absorbent nonwoven fabric to form A layer, and the liquid-absorbent surface material is laminated on A layer. Then, the laminated body is heated and pressurized so as to produce the liquid-absorbent sheet.

The interface between the liquid-absorbent surface material layer and A layer and the interface between B layer and the liquid-absorbent rear material layer are thermally fused using heating and pressing rollers. At this time, the SAP is plasticized with the moisture contained therein and serves as a binder. When the thermally fusible synthetic fiber is contained in the liquid-absorbent nonwoven fabric layer, the liquid-absorbent surface material and the liquid-absorbent rear material are adhered more tightly. This is done by using the rollers to heat and pressurize both of the liquid-absorbent surface material layer and the liquid-absorbent rear material layer at the temperature not lower than the temperature at which the surface of the thermally fusible synthetic fiber melts. Furthermore, this adherence is achieved due to the effect of tangled molecules of plasticized thermally fusible synthetic fiber and the SAP plasticized with the moisture contained therein. In order that the adhesive strength between the liquid-absorbent surface material and the liquid-absorbent rear material be enhanced, a small amount of the moisture is preferably supplied to the liquid-absorbent surface material and the liquid-absorbent rear material. Alternatively, thermally fusible powders or spray adhesives may be applied so as to increase the adhesive strength. Since the thermal fusing step using the heating and pressing rollers welds the SAP layers and the liquid-absorbent nonwoven fabric again, it is possible to adjust the thickness of the liquid-absorbent sheet at the same time.

In order to further improve the liquid diffusion properties, the high-density portion and the low-density portion may be alternately arranged on the liquid-absorbent sheet by treating sheet using the heating and pressing emboss rollers with longitudinal stripes or meshes engraved on one or both rollers.

In order to enhance the adhesive strength between the liquid-absorbent surface material layer and A layer or between the liquid-absorbent rear material layer and B layer, and also to prevent the SAP from unevenly distributing during preparation, the SAP is preferably made to be intermingled with the liquid-absorbent surface material layer or the liquid-absorbent rear material layer in at least a partial area of the interface between A layer and the liquid-absorbent surface material layer or the interface between B layer and the liquid-absorbent rear material layer.

The liquid-absorbent sheet according to the present invention may be used as an absorbent body in an absorbent article composed of a liquid-permeable top sheet, an absorbent body, and a liquid-impermeable back sheet, or an absorbent body in an absorbent article composed of a liquid-permeable top sheet, a sublayer, an absorbent body, and a liquid-impermeable back sheet. Also, the liquid-absorbent sheet according to the present invention may be used as an absorbent body in an absorbent article composed of a sublayer, a liquid-permeable top sheet, an absorbent body, and a liquid-impermeable back sheet.

In this usage, the liquid-absorbent sheet according to the present invention is used by placing the liquid-absorbent surface material layer on the top sheet side.

The liquid-absorbent sheet according to the present invention may be used for disposable diapers, sanitary napkins, breast milk pads, water-absorbent sheets, oil-absorbent sheets, pads aiming at absorbing a liquid with a viscosity such as an ink jet printer ink effluent, various wipes, or the like.

EXAMPLES

In the following, although the present invention will be more specifically explained by way of examples, it is apparent that the present invention is not limited to these. Also, "parts" and "%" used in the examples indicate "parts by mass" and "% by mass" unless otherwise so indicated.

Example 1

On a wire, a tissue having a basis weight of 14 m² (manufactured by Nippon Tokushu Fabric Co., Ltd.) was unwinded as a liquid-absorbent rear material, and 125 g/m² of a SAP (super absorbent polymer manufactured by SUMITOMO SEIKA CHEMICALS CO., LTD., under the trademark of AQUA KEEP SA 60 SX) was sprayed onto the rear material tissue using a powder feeder, and thus B layer was formed on the rear material tissue layer. Onto B layer, an air laid nonwoven fabric composed of 205 g/m² of a pulp fiber with a fiber length of 0.05 to 5 mm (softwood bleached kraft pulp (NBKP) manufactured by Oji Paper Co., Ltd.) and 17 g/m² (content ratio: 7.7% by mass) of a PE/PP (core/sheath) fiber with a fineness of 1.7 dtex and a length of 5 mm (manufactured by CHISSO CORPORATION under the trade name of ESC) was laminated using a mat former, and thus the air laid nonwoven fabric layer was formed on B layer. Then, 125 g/m² of the SAP was sprayed onto the air laid nonwoven fabric layer using a powder feeder, and thus A layer was formed on the air laid nonwoven fabric layer. Then, a tissue with a basis weight of 14 g/m² (manufactured by Nippon Tokushu Fabric Co., Ltd.) was laminated on A layer as a liquid-absorbent surface material layer, and then the resultant was passed through a drier to obtain an absorbent sheet composed of five layers, that is, the surface material layer, A layer, the air laid nonwoven fabric layer, B layer, and the rear material layer. Both surfaces of this absorbent sheet were treated using heating and pressing rollers so that the surface material layer and the rear material layer were adhered to be fixed. Thus, a liquid-absorbent sheet with a basis weight of 500 g/m² and a thickness of 2.8 mm was obtained.

Example 2

A liquid-absorbent sheet with a basis weight of 500 g/m² and a thickness of 2.4 mm was produced in a similar manner to that of Example 1 except that an absorbent sheet composed of five layers, that is, a surface material layer, A layer, an air laid nonwoven fabric layer, B layer, and a rear material layer was prepared as described below. On a wire, the tissue having a basis weight of 14 g/m² was unwound as the rear material layer, and 85 g/m² of the SAP was sprayed onto the rear material layer using a powder feeder, and thus B layer was formed on the rear material layer. Onto B layer, an air laid nonwoven fabric composed of 205 g/m² of the pulp fiber with a fiber length of 0.05 to 5 mm (NBKP manufactured by Oji Paper Co., Ltd.), 17 g/m² (content ratio: 7.7% by mass) of the PE/PP (core/sheath) fiber with a fineness of 1.7 dtex and a length of 5 mm, and 85 g/m² of the SAP was laminated using a mat former, and thus the air laid nonwoven fabric layer was formed on B layer. Then, 80 g/m² of the SAP was sprayed onto the air laid nonwoven fabric layer using a powder feeder, and thus A layer was formed on the air laid nonwoven fabric layer. Then, the tissue with a basis weight of 14 g/m was laminated on A layer as the surface material layer. Then, the resultant was passed through a drier to obtain the absorbent sheet.

Example 3

A liquid-absorbent sheet with a basis weight of 500 g/m² and a thickness of 2.9 mm was obtained in a similar manner to that of Example 1 except that an absorbent sheet composed of five layers, that is, a surface material layer, A layer, an air laid nonwoven fabric layer, B layer, and a rear material layer was prepared as described below. On a wire, the tissue having a basis weight of 14 g/m² was unwinded as the rear material layer, and 125 g/m² of the SAP was sprayed onto the rear material layer using a powder feeder, and thus B layer was formed on the rear material layer. Onto B layer, an air laid nonwoven fabric composed of 205 g/m² of the pulp fiber with a fiber length of 0.05 to 5 mm (NBKP manufactured by Oji Paper Co., Ltd.), 17 g/m² (content ratio: 7.7% by mass) of the PE/PP (core/sheath) fiber with a fineness of 1.7 dtex and a length of 5 mm, and 50 g/m² of the SAP was laminated using a mat former, and thus the air laid nonwoven fabric layer was formed on B layer. Then, 75 g/m² of the SAP was sprayed onto the air laid nonwoven fabric layer using a powder feeder, and thus A layer was formed on the air laid nonwoven fabric layer. Then, the tissue with a basis weight of 14 g/m² was laminated on A layer as the surface material layer. Then, the resultant was passed through a drier to obtain the absorbent sheet.

Example 4

A liquid-absorbent sheet with a basis weight of 526 g/m² and a thickness of 2.7 mm was obtained in a similar manner to that of Example 1 except that an air laid nonwoven fabric mainly containing a pulp with a basis weight of 40 g/m² (KINOCLOTH manufactured by OJI KINOCLOTH Co., LTD.) was used instead of the tissue as the surface material.

Example 5

A liquid-absorbent sheet with a basis weight of 500 g/m² and a thickness of 2.4 mm was obtained in a similar manner to that of Example 2 except that the surface material layer-side surface of the absorbent sheet was treated using heating and pressing rollers, one of which has stripes with intervals of 2 mm, the stripes being engraved in a longitudinal direction with respect to the width direction of the roller, so that the surface material layer-side surface has dents and salients with vertical differences of 0.4 mm and the thickness of the surface material layer at the dent is 2.0 mm.

Comparative Example 1

On a wire, the tissue having a basis weight of 14 g/m² was unwinded as a rear material layer, onto which an air laid nonwoven fabric composed of 189 g/m² of the pulp fiber with a fiber length of 0.05 to 5 mm (NBKP manufactured by Oji Paper Co., Ltd.) and 33 g/m² (content ratio: 15% by mass) of the PE/PP (core/sheath) fiber with a fineness of 1.7 dtex and a length of 5 mm was laminated using a mat former. Then, 250 g/m² of the SAP was sprayed onto the air laid nonwoven fabric layer using a powder feeder. Then, the tissue with a basis weight of 14 g/m² was laminated on the SAP layer as a surface material layer, and then the resultant was passed through a drier to obtain an absorbent sheet composed of the surface material, the SAP layer, the air laid nonwoven fabric layer, and the rear material layer. Both surfaces of this absorbent sheet were further treated using heating and pressing rollers to be adhered and fixed. Thus, a liquid-absorbent sheet with a basis weight of 500 g/m² and a thickness of 2.0 mm was obtained.

Comparative Example 2

On a wire, the tissue having a basis weight of 14 g/m² was unwinded as a rear material layer, onto which an air laid nonwoven fabric composed of 205 g/m² of the pulp fiber with a fiber length of 0.05 to 5 mm (NBKP manufactured by Oji Paper Co., Ltd.), 17 g/m² (content ratio: 7.7% by mass) of the PE/PP (core/sheath) fiber with a fineness of 1.7 dtex and a length of 5 mm was laminated using a mat former. Then, 125 g/m² of the SAP was sprayed onto the air laid nonwoven fabric layer using a powder feeder. Then, the tissue with a basis weight of 14 g/m² was laminated on the SAP layer as the surface material layer, and then the resultant was passed through a drier to obtain an absorbent sheet composed of the surface material, the SAP layer, the air laid nonwoven fabric layer, and the rear material layer. Both surfaces of this absorbent sheet were further treated using heating and pressing rollers to be adhered and fixed. Thus, a liquid-absorbent sheet with a basis weight of 500 g/m² and a thickness of 2.8 mm was obtained.

Comparative Example 3

A liquid-absorbent sheet with a basis weight of 430 g/m² and a thickness of 2.8 mm was obtained in a similar manner to that of Example 1 except that the amount of the SAP sprayed onto the rear material layer was 90 g/m² and the amount of the SAP sprayed onto the air laid nonwoven fabric layer was 90 g/m².

Comparative Example 4

A liquid-absorbent sheet with a basis weight of 500 g/m² and a thickness of 2.4 mm was obtained in a similar manner to that of Example 2 except that the amount of the SAP sprayed onto the rear material layer was 50 g/m², the amount of the SAP contained in the air laid nonwoven fabric layer was 150 g/m², and the amount of the SAP sprayed onto the air laid nonwoven fabric layer was 50 g/m².

Comparative Example 5

A liquid-absorbent sheet with a basis weight of 500 g/m² and a thickness of 2.8 mm was obtained in a similar manner to that of Example 1 except that the amount of the SAP sprayed onto the rear material layer was 200 g/m² and the amount of the SAP sprayed onto the air laid nonwoven fabric layer was 50 g/m².

The liquid-absorbent sheets obtained as described above were evaluated in accordance with the following methods, and results thereof are shown in Table 1.

Preparation of Samples to be Evaluated

Each liquid-absorbent sheet obtained above was cut into a sheet-shaped piece with a width of 100 mm and a length of 250 mm. On the surface material layer-side surface of the piece, a perforated sheet with a basis weight of 27 g/m² was laminated as a top sheet. On the rear material layer-side surface of the piece, a back sheet with a basis weight of 20 g/m² was laminated. Thus, an absorbent article was obtained as each sample and evaluated in accordance with the following.

Preparation of Test Solution 0.9% by mass of physiological saline in which 9 g of sodium chloride was dissolved in 991 g of distilled water was colored with a coloring agent (blue food color No. 1 manufactured by Benifuji Chemical Industry Co., Ltd.) so as to visually observe effects of the samples, and used as a test solution.

Test with Respect to Absorbent Rate

A special apparatus 4 shown in FIG. 1 was used for measuring the absorbent rate of each samples. The apparatus 4 was composed of a metal plate (weight) 1 and an acrylic tube 3. The metal plate 1 had a width of 80 mm, a length of 80 mm, a thickness of 10 mm, and a weight of 397.7 g. In the center portion of the metal plate 1, a hole 2 with a diameter of 41 mm was formed. The acrylic tube 3 had a diameter of 30 mm, a height of 130 mm, and a weight of 89.2 g. In order to use the apparatus 4, the metal plate 3 was placed on the surface of the sample (not shown in FIG. 1), and then the acrylic tube 3 was placed in the hole 2 of the plate 3 to make contact with the sample. Then, 80 cc of the test solution was applied onto the sample through the acrylic tube and the time required for the test solution to be completely absorbed in the sample was measured. Each sample was tested three times with intervals of 30 minutes and measured with respect to the absorbent rate of each time.

Test with Respect to Liquid Diffusion Properties

After every measurement of the absorbent rate as described above, the apparatus 4 was removed from the sample, the longitudinal diffusion length of the test solution spread on the sample was measured, and the occurrence of side leakage was checked. Since these steps were conducted after every measurement of the absorbent rate, these steps were conducted three times per sample with intervals of 30 minutes.

Wet-Back

When the test solution was completely diffused, that is, 10 minutes after every measurement of the absorbent rate, a filter paper (No. 2) was placed onto the entire surface of the sample, and then a 3.5-kg weight was placed on the filter paper so that the load was evenly applied thereon. 30 seconds after placing the weight, the mass of the test solution absorbed in the filter paper was measured.

Total Evaluation

Each sample was comprehensively evaluated from the standpoint of usage as a liquid-absorbent sheet.
 A: Very excellent as a liquid-absorbent sheet.
 B: Excellent as a liquid-absorbent sheet.
 C: There was a slight problem under a level having no trouble in practical use as a liquid-absorbent sheet.
 D: There were problems under a level unpractical as a liquid-absorbent sheet.
 E: Very inferior as a liquid-absorbent sheet.

TABLE 1

|  | Basis weight (g/m²) | Thickness (mm) | Absorbent rate (seconds) first/second/third Evaluation | Diffusion length (mm) first/second/third Occurrence of side leakage | Wet-back (g) first/second/third Evaluation | Total evaluation |
|---|---|---|---|---|---|---|
| Example 1 | 500 | 2.8 | 106/102/120 B | 139/185/250 B | 0.15/1.15/5.49 B | B |
| Example 2 | 500 | 2.4 | 75/64/64 B | 168/250/250 B | 0.19/2.65/8.89 B | B |
| Example 3 | 500 | 2.9 | 101/104/114 B | 133/216/250 B | 0.34/2.68/8.66 B | B |
| Example 4 | 526 | 2.7 | 75/58/75 B | 155/203/250 B | 0.06/0.59/5.21 B | A |
| Example 5 | 500 | 2.4 | 111/137/150 B | 250/250/250 B | 0.27/2.45/7.35 B | B |
| Comparative Example 1 | 500 | 2.0 | 131/163/211 D | 158/250/250 D | 0.39/6.69/28.0 D | E |
| Comparative Example 2 | 500 | 2.8 | 93/125/178 C | 180/250/250 B | 0.15/2.13/24.5 D | D |
| Comparative Example 3 | 430 | 2.8 | 100/128/161 C | 137/175/250 D | 0.15/2.30/17.4 D | D |
| Comparative Example 4 | 500 | 2.4 | 85/92/172 C | 145/250/250 D | 0.20/2.20/26.5 D | D |
| Comparative Example 5 | 500 | 2.8 | 63/110/181 C | 128/225/250 D | 0.23/7.23/18.4 D | D |

As shown in Table 1, the liquid-absorbent sheets prepared in Examples 1 to 5 were thin, rapidly absorbed liquid, and exhibited less wet-back and side leakage. On the other hand, the liquid-absorbent sheets prepared in Comparative Examples 1 to 5 were particularly inferior in terms of the liquid-absorbability and wet-back preventability.

As described above, the liquid-absorbent sheet according to the present invention has a thin thickness, a rapid absorbent rate, and a high wet-back preventability, and so can effectively absorb and hold the fluid excreted from the human body as compared with conventional absorbent sheets. Since the liquid-absorbent sheet according to the present invention is compact and excellent in the liquid absorbability, it can be preferably used as a liquid-absorbent sheet composing an absorbent article such as a paper diaper, sanitary napkin, or the like.

What is claimed is:

1. A liquid-absorbent sheet comprising:
    a liquid-absorbent surface material comprising a pulp;
    a liquid-absorbent nonwoven fabric;
    a liquid-absorbent rear material comprising a pulp;
    a super absorbent polymer;
    an A layer which is disposed between the liquid-absorbent surface material and the liquid-absorbent nonwoven fabric; and
    a B layer which is disposed between the liquid-absorbent nonwoven fabric and the liquid-absorbent rear material,
    wherein the total amount of the super absorbent polymer is 200 to 400 g/m², which is allocated in the A layer at 30 to 50% by mass, the liquid-absorbent nonwoven fabric layer at 0 to 40% by mass, and the B layer at 30 to 70% by mass; and wherein
    the content ratio of the super absorbent polymer in the A layer is less than or equal to the content ratio of the super absorbent polymer in the B layer.

2. A liquid-absorbent sheet according to claim 1, wherein the liquid-absorbent nonwoven fabric is a hydrophilic air laid nonwoven fabric.

3. A liquid-absorbent sheet according to claim 1, wherein the liquid-absorbent nonwoven fabric comprises a pulp and a thermally fusible synthetic fiber, and the content ratio of the thermally fusible synthetic fiber is 0.1 to 15% by mass with respect to the total mass of the nonwoven fabric excluding the super absorbent polymer.

4. A liquid-absorbent sheet according to claim 1, wherein the liquid-absorbent surface material layer and the A layer, or the B layer and the liquid-absorbent rear material layer are partially intermingled.

5. A method for producing the liquid-absorbent sheet of claim 1, comprising:
    thermally fusing an interface between the liquid-absorbent surface material layer and the A layer and an interface between the liquid-absorbent rear material layer and the B layer using heating and pressing rollers.

* * * * *